(12) United States Patent
Grenier et al.

(10) Patent No.: US 8,537,355 B2
(45) Date of Patent: Sep. 17, 2013

(54) METHOD AND DEVICE FOR MEASURING A CHEMICAL COMPOSITION OF A LIQUID METAL SUITABLE FOR COATING A STEEL STRIP

(75) Inventors: Benjamin Grenier, Saint-Paul-en-Jarez (FR); Marc Michaut, L'Horme (FR)

(73) Assignee: Siemens VAI Metals Technologies SAS, Saint-Chamond (FR)

( * ) Notice: Subject to any disclaimer, the term of this patent is extended or adjusted under 35 U.S.C. 154(b) by 198 days.

(21) Appl. No.: 13/129,476

(22) PCT Filed: Nov. 14, 2008

(86) PCT No.: PCT/FR2008/001608
§ 371 (c)(1),
(2), (4) Date: May 16, 2011

(87) PCT Pub. No.: WO2010/055212
PCT Pub. Date: May 20, 2010

(65) Prior Publication Data
US 2011/0222057 A1    Sep. 15, 2011

(51) Int. Cl.
*G01J 3/30*    (2006.01)
(52) U.S. Cl.
USPC .......................................... 356/318
(58) Field of Classification Search
USPC .................................. 356/311, 318
See application file for complete search history.

(56) References Cited

U.S. PATENT DOCUMENTS

| 4,995,723 | A | 2/1991 | Carlhoff et al. |
| 6,172,367 | B1 | 1/2001 | Fritz et al. |
| 2002/0159059 | A1 | 10/2002 | Sabsabi et al. |
| 2003/0234928 | A1 | 12/2003 | Lucas et al. |
| 2009/0308499 | A1 * | 12/2009 | Scott et al. ..................... 148/500 |

FOREIGN PATENT DOCUMENTS

| DE | 4443407 A1 | 6/1995 |
| EP | 0362577 A2 | 4/1990 |
| RU | 2163713 C2 | 2/2001 |
| RU | 2200207 C2 | 3/2003 |
| RU | 2273841 C1 | 4/2006 |
| RU | 2303255 C1 | 7/2007 |
| WO | 02063284 A2 | 8/2002 |
| WO | 2008067620 A1 | 6/2008 |

* cited by examiner

*Primary Examiner* — Tarifur Chowdhury
*Assistant Examiner* — Abdullahi Nur
(74) *Attorney, Agent, or Firm* — Laurence A. Greenberg; Werner H. Stemer; Ralph E. Locher

(57) ABSTRACT

A method and a device measure a chemical composition of a liquid metal suitable for coating a steel strip. The method measures a chemical composition of a liquid metal suitable for coating a steel strip for which the liquid metal is formed continuously in a first cavity, and the composition of the liquid metal is measured on a direct measurement surface thereof, for which a specimen of the liquid metal reaching the measurement surface is heated to a chosen temperature so as to isolate principally iron-based impurities from the measurement surface. Several embodiments of devices suitable for implementing the method are also presented.

22 Claims, 2 Drawing Sheets

METHOD AND DEVICE FOR MEASURING A CHEMICAL COMPOSITION OF A LIQUID METAL SUITABLE FOR COATING A STEEL STRIP

BACKGROUND OF THE INVENTION

Field of the Invention

The present invention relates to a method and a device for measuring a chemical composition of a metal melt for coating a steel strip as claimed in the preambles to claims 1 and 2.

A main context of the invention relates to baths for hot-dip metal coating of steel strips, particularly to the chemical analysis of said coating baths.

By metal coating is meant all types of metal alloy designed to improve the corrosion resistance of the steel strips. In particular, but not in a limiting sense, it is taken to mean galvanizing alloys composed mainly of zinc and aluminum.

Measuring the chemical composition of the galvanizing baths is particularly necessary in order to adjust the content of at least one alloying material using, for example, ingots of appropriate composition introduced in an appropriate sequence into a molten bath of coating metal. It uses measurement techniques on samples taken from the bath, solidified into mini-ingots then analyzed by spectroscopy. Although this method is reliable, it has the disadvantage of being slow which makes it impossible to react quickly e.g. by modifying, the supply of alloy ingots to the bath. On the other hand, the task of manually taking samples from the molten bath exposes the operators to hazardous conditions.

Similar measurements using electrochemical sensors have also been proposed such as that described in the document U.S. Pat. No. 5,256,272. However, these sensors are fragile and their calibration must be frequently checked by comparative analyses with the old methods of manual sampling and analysis of mini-ingots.

Other measuring methods providing real time analysis have been proposed, based around a process of spectroscopic analysis by laser ablation, more commonly known as "Laser Induced Breakdown Spectroscopy" or LIBS. Such a method consists of directing at the target to be analyzed a very narrow laser beam powerful enough for a very brief shot to be sufficient to generate a plasma whose radiation is subjected to spectral analysis. The use of such a method for molten metal baths is envisioned in the application WO 02/063284 which proposes carrying out the analysis of the bath on the surface of a molten sample circulating in or brought into a measurement cell.

Now, especially in the case of galvanization of steel strips using alloys of zinc and aluminum, this type of surface measurement of a molten sample is prone, on the one hand, to a risk of surface oxidation and, on the other, to the presence of intermetallic compounds of iron, aluminum and zinc known as dross, the aluminum and zinc contents of which are very different from the average content of the bath in which they form. Indeed, contact with the molten metal mixture causes the iron in the surface of the steel strip to dissolve. This dissolved iron contributes on the one hand to the formation on the surface of the strip of a very thin layer of $Fe_2Al_5Zn_x$ and, on the other, diffuses into the molten metal bath unless the layer of $Fe_2Al_5Zn_x$ is formed continuously. The $Fe_2Al_5Zn_x$ serves as a base for the protective zinc layer whereas the iron diffused into the bath will contribute to the formation of particles of intermetallic compounds of Fe, Al and Zn ranging in size from a few microns to a few tens of microns.

The germination and growth kinetics of these intermetallic compounds in the galvanizing baths will be familiar to the average person skilled in the art. Depending on the temperature of the bath of molten zinc and its aluminum content, the amount of iron capable of being dissolved varies between fairly wide limits. If the diffused iron content exceeds the solubility limit, nucleation and swelling of intermetallic compounds becomes possible. In the usual continuous galvanizing processes, the coating bath is always saturated with iron, which means that all the iron dissolved from the strip and diffused into the molten mixture is available for the creation within the molten bath of particles of intermetallic compounds whose size can attain several tens of microns. Depending on their composition which determines their density, some of these particles settle to the bottom of the pot or mostly float on the surface of the molten bath, and are thus usually referred to as bottom or top dross.

The presence of these intermetallic compounds in the sample, particularly on its surface, is therefore likely to invalidate the analysis by producing concentrations of the different constituents measured—e.g. zinc, aluminum and iron—that are different from those of the bath itself.

Application WO 2008/067620 proposes to solve the problems posed by the particles of intermetallic compounds known as "top dross" which float on the surface of the molten bath by using a system of automatic surface inspection allowing the presence of dross on the molten bath to be detected, thus ensuring that a LIBS type analyzer is aimed at dross-free areas, or triggering the operation of a dross skimming device in order to clear the surface of the bath. However, this cumbersome and complex video-based method of surface monitoring can prove to be too inaccurate (if not impossible in the case of full dross cover) to guarantee that the ablation laser shot is not directed at dross that is too discrete to be identified as such by the image processing systems.

BRIEF SUMMARY OF THE INVENTION

One object of the present invention is therefore to propose a method and a device for measuring a chemical composition of a metal melt for coating a steel strip, wherein direct measurement of a metal melt sample is qualitatively improved.

Based on a method for measuring a chemical composition of a metal melt for coating a steel strip in a continuous line, wherein the metal melt is formed continuously in a first cavity and its composition is measured on a direct measurement surface of said melt, the invention provides that a metal melt sample reaching the measurement surface is subjected to a temperature selected so as to isolate mainly iron-based impurities from said measurement surface.

The terminology of direct surface measurement signifies in particular that a chemical composition analyzing means (such as a laser beam of a LIBS) performs its physical measurement in direct incidence on the locally predefined measurement surface. As said measurement surface is free of impurities when the sample to be measured reaches it in accordance with the invention, it is therefore advantageously no longer necessary to look for a measurement surface apparently free of impurities using complex means of detection that are very often too inaccurate.

In other words, the method according to the invention is characterized in that the sample of a molten alloy, prior to measurement of its composition for the analysis thereof, is generally undergoes reheating in order to redissolve into the molten bath iron-based intermetallic compounds present in the form of impurities, thereby preserving only the wanted composition in the direct measurement surface or volume.

The reheating is thus carried out up to said temperature selected so as to ensure homogeneity of the molten bath and sufficient solubility of the iron compared to the impurities, taking into account the composition of the alloy.

Indeed, in the case of alloys of zinc and aluminum, and for a given aluminum content, the solubility limit of the iron in the molten mixture increases with temperature. For example, for an aluminum content of around 0.20%, the transition from a temperature of 460° C.—the usual temperature of a galvanizing bath of this kind—to 480° C., almost doubles the solubility limit of the iron. An even higher temperature, e.g. selected according to the invention between 500° C. and 600° C., then ensures solubility of the iron at content levels greater than those normally encountered under supersaturated conditions in galvanizing baths. This permits complete redissolving of the impurities (out of the sample locally reaching the direct measurement surface) resulting from the intermetallic compounds which are, therefore, no longer likely to interfere with the analysis by the measuring instrument for analysis aimed at said surface.

The invention also provides a device for implementing the above described method according to the invention.

Generally speaking, based on a device for measuring a chemical composition of a metal melt suitable for coating a steel strip in a continuous line, said device according to the invention comprises:

a first cavity containing the metal melt, an instrument for measuring the composition of the metal melt on a direct measurement surface of said melt, and is characterized in that a temperature regulator is disposed in the vicinity of the measurement surface so as to isolate mainly iron-based impurities from a sample of metal melt reaching said measurement surface.

A number of sub-claims likewise set out advantages of the invention.

Embodiments of the device according to the invention will now be presented, two examples of which are described with reference to the accompanying drawings:

DESCRIPTION OF THE INVENTION

Figure 1:
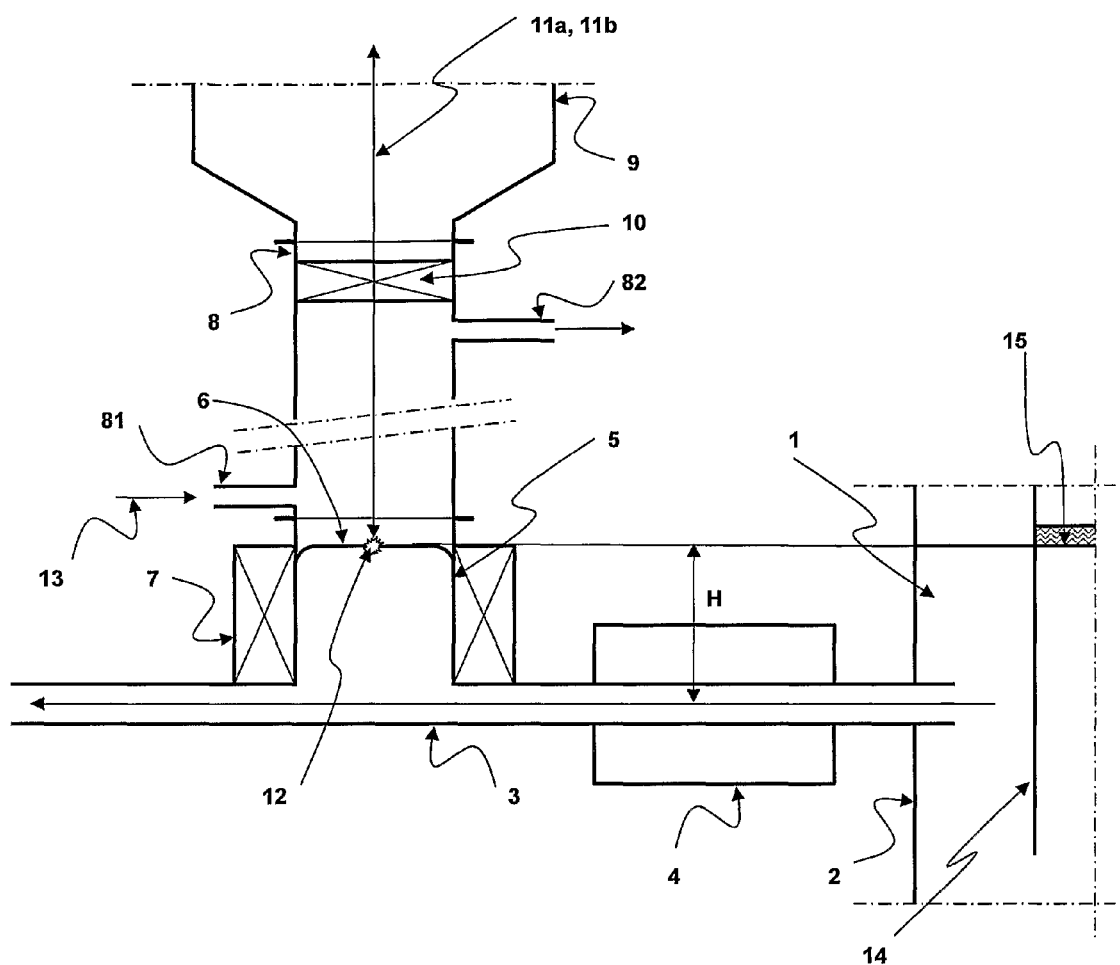
FIG. 1 Schematic diagram of a first embodiment of the device according to the invention, FIG. 2 Schematic diagram of a second embodiment of the device according to the invention.

FIG. 1 shows a schematic diagram of a first embodiment of the device according to the invention.

Said device for measuring a chemical composition of a metal melt (1) is designed for a continuous steel strip coating line (not shown) and comprises:

a first cavity (2) containing the metal melt, a measuring instrument (9) for measuring the composition of the metal melt on a direct measurement surface (6) of said melt, a temperature regulator (7) being disposed in the vicinity of the measurement surface (6, 12) so as to isolate mainly iron-based impurities from a sample (5) of metal melt reaching said measurement surface.

In this example, the direct measurement surface is located on a circulation circuit (3) of the metal melt of the first cavity, said circuit having a circulation intake ideally disposed at a height level of the cavity (2) such that most impurities, such as top and bottom dross, are kept away from said circuit (3).

The first cavity can be here a coating pot and the circulation circuit (3) can then comprise a loop disposed externally to said pot.

The circulation circuit (3) can alternatively comprise a metal melt circulating channel inside or at least attached to the first cavity, said channel being ideal for induction heating of the molten metal bath. This enables the circulation infrastructure of the sample to be measured as far as the direct measurement surface to be very simply implemented, as it only requires a single measurement chamber (5) to be disposed laterally to the heating channel in order to be able to introduce a direct measurement beam therein.

The solubility of the iron is intrinsically achieved in the heating channel, if necessary by adding a suitable induction unit in order to attain there a temperature well chosen locally to achieve the object of the invention.

The first cavity can also be at least one pot for melting metal alloys to prepare the metal melt, said melting pot being connected to a second cavity such as a coating pot (of the kind described above) and the circulation circuit (3) is connected to a metal melt conduit between the first and the second cavity. Such a multi-cavity arrangement generally allows better isolation of most of the dross as well as better regulation of the temperatures of the different baths (melting/coating).

In the example in FIG. 1, a molten coating metal (1) can thus be contained in a pot (2) used for coating a steel strip or for the required melting of ingots to produce the composite constitution of said metal melt (1).

The molten metal circulation circuit (3) is used to transfer molten metal between the ingot melting pot and the separate strip coating pot or to provide a sample and return circulation loop to one of said pots (2). Said circulation can be gravity-fed or forced via at least one pump (4) disposed upstream of the circulation circuit (3).

A measurement chamber (5) is attached to one side of the circulation circuit (3) and receives a quantity of molten metal delimited by said direct measurement surface (6) (free from impurities) located at a height (H) corresponding to the free surface of the molten bath of the initial cavity (2) in the case of a gravity-fed circulation circuit or corresponding to the lifting capacity of the pumping device in the case of forced circulation.

A single-phase or polyphase AC induction heating device (7) is used to heat the cavity (5) in order to be able to regulate the temperature of a sample of metal melt circulating therein and therefore inventively remove undesirable impurities from the sample.

A casing (8) provides the leakproof junction between the measurement chamber (5) and an analyzing instrument (9) such as a LIBS. It comprises, on the measuring instrument (9) side, a window (10) transparent to the ablation laser beam (11a) from the analyzing instrument and transparent to the radiation (11b) of the plasma (12) generated by said beam on the direct measurement surface (6) of the metal melt. The casing (8) has orifices (81; 82) to allow scavenging (13) by a neutral gas such as nitrogen between the surface of the molten metal (6) and the window (10). This enables surface oxidation of the metal melt to be prevented in order to ensure better measurement of the composition thereof.

A sampling orifice of the circulation circuit (3) in the wall of the cavity (2) is located downstream of a baffle (14) in said cavity capable of retaining the particles of intermetallic compounds (15) floating on the surface of the bath (1).

Figure 2:
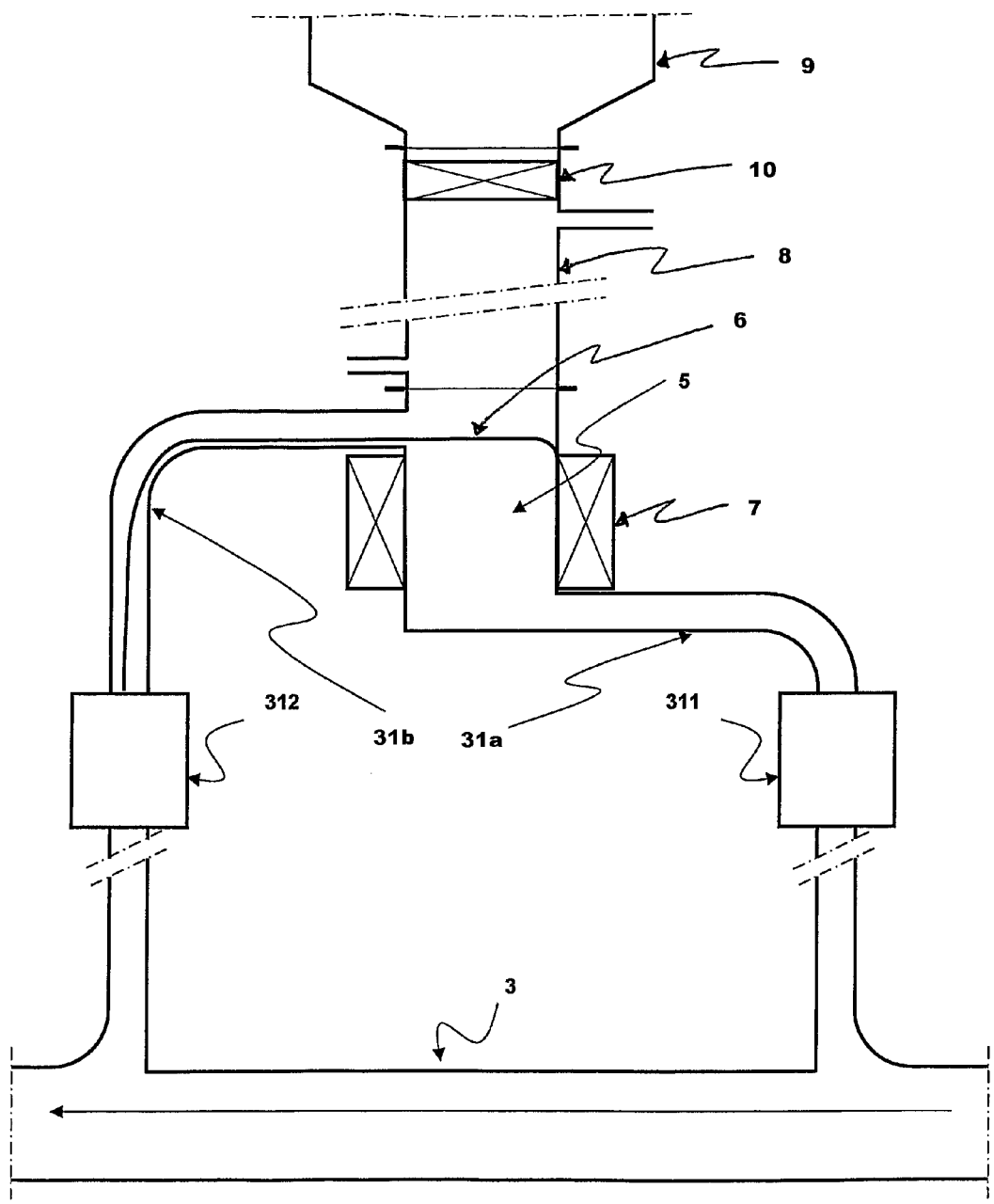

FIG. 2 shows a schematic diagram of a second embodiment of the device according to the invention. Unlike in FIG. 1, the circulation circuit (3) comprises a bypass in the form of a vertical riser (8, 31a) of a height at least greater than the melt level in the first cavity (not shown, but possibly identical to that in FIG. 1) and the direct measurement surface (6) is defined by the melt level in said riser. The vertical riser (31a) is connected to a vertical downpipe (31b) returning into the circulation circuit (3) according to the circulation direction of said circuit. Each of the pipes (31a, 31b) comprises an e.g. electromagnetic valve (311, 312) in order to temporarily block off the melt in the bypass in the measurement chamber (5). More precisely, at least one of the valves (311, 312) is subject to a defined blocking delay to ensure heating of sufficient duration and therefore sufficient isolation of the impurities from the measurement surface, following which a measuring phase is initiated and the measurement quality is therefore improved. Other advantages are also associated with this aspect, namely: the ability to permit, under this delay, better mixing of the melt to be measured, particularly if the means of heating comprises an electromagnetic induction element; finally depending on requirements of the surface composition measuring instrument, in order to immobilize the sample to be measured to perform a measurement under mechanically if not optically stable conditions if the measuring instrument requires optical adjustment. For returning the metal melt to the circulation circuit (3), the vertical downpipe (31b) comprises a melt overflow inlet on a wall of the measurement chamber (5). This overflow also constitutes a simple means of fixing the height level of the direct measurement surface in order advantageously to avoid any optical readjustment to said surface.

As in FIG. 1, a temperature regulator (7) according to FIG. 2 is disposed on at least one part subjacent to the measurement surface, ideally to the means of induction heating such as a single-phase AC system producing only moderate mixing of the melt or a polyphase AC system producing significant mixing of the melt. Similarly, although not shown, in the first cavity, intake of metal melt by the circulation circuit (3) is preceded by a baffle device for catching at least compounds floating on the surface of the molten bath sampled in the first cavity. Likewise, a circulation circuit of an inert gas is applied to the direct metal melt measurement surface to protect it from oxidation reactions, the circulation flowrate of which ensures leakproof scavenging between the measurement chamber (5) comprising the direct measurement surface (6) and the measuring instrument (9) facing said surface. Similarly to FIG. 1, a window (10) of a material transparent to an ablation laser beam and to plasma radiation can be disposed between the measuring instrument and the direct measurement surface (6) so as to form a leakproof measurement chamber (5).

In all the embodiments of the device according to the invention:
the measuring instrument is a spectral analysis device using laser ablation of the direct measurement surface (6), but can be another prior art measuring system.
the direct measurement surface (6) is ideally located in a measurement chamber (5) made of materials that are unreactive with the metal melt, such as an austenitic stainless steel, a ceramic or a ceramic-coated metal.

It should also be noted that the circulation circuit (3) according to FIG. 1 or 2 can comprise a pump for sampling the metal melt at least at its intake. The type of pump can be electromagnetic, mechanical (e.g. of the centrifugal type) or pneumatic (by means of e.g. Venturi effect pump priming).

The pump thus provides a circulation. If it is electromagnetic, it contributes at least partially to inductive heating of the melt so as to raise the solubility threshold of the iron and therefore to isolate impurities from a sample circulating there as provided by the invention. Thus, the circulation circuit (3) can comprise a pump whose pumping properties are linked to the isolation of impurities, ideally in the case of an electromagnetic pump or also in the case of a pump equipped with an overflow stage for physically separating the metal melt from the impurities.

Finally and in particular for FIG. 3, a variant of the device according to the invention can provide that the circulation circuit (3) comprises at least one intake such as a pipe or a sampling branch designed to be dipped through the molten metal surface in the cavity. In other words, the complete composition measuring device is made movable and therefore positionable in the cavity, forming a sampling branch such as the pipe (31a) and a return flow branch such as the pipe (31b).

The invention claimed is:

1. A device for measuring a chemical composition of a metal melt suitable for coating a steel strip, the device comprising:
a first cavity containing the metal melt;
a measuring instrument for measuring the chemical composition of the metal melt by measuring a direct measurement surface of the metal melt;
a temperature regulator disposed in a vicinity of the direct measurement surface so as to isolate mainly iron-based impurities from a sample of the metal melt reaching the direct measurement surface; and
a circulation circuit, the direct measurement surface being disposed on said circulation circuit for the metal melt of said first cavity, said circulation circuit having a circulation intake disposed at a height level of said first cavity such that most impurities, including a top dross and a bottom dross, are kept away from said circulation circuit.

2. The device as claimed in claim 1, wherein said first cavity is a coating pot and said circulation circuit has a loop disposed externally to said coating pot.

3. The device according to claim 2, wherein said circulation circuit has a bypass in a form of a vertical riser of a height at least greater than a melt level in said first cavity and the direct measurement surface is defined by the melt level in said vertical riser.

4. The device according to claim 3, further comprising a vertical downpipe, said vertical riser is connected to said vertical downpipe terminating in said circulation circuit.

5. The device according to claim 4, wherein each of said downpipe and said vertical riser has a valve to temporarily block off the metal melt in a bypass.

6. The device according to claim 5, wherein at least one of said valves is subject to a defined blocking delay to ensure sufficient isolation of the impurities from the direct measurement surface, following which a measuring phase is initiated.

7. The device according to claim 4, wherein said vertical downpipe has a melt overflow intake.

8. The device according to claim 4, wherein said temperature regulator is disposed on a least one part subjacent to the direct measurement surface.

9. The device according to claim 4, further comprising an induction heater selected from the group consisting of a single-phase AC system producing only a moderate mixing of the metal melt and a polyphase AC system producing a significant mixing of the metal melt, said temperature regulator is disposed on a least one part subjacent to said direct measurement surface and to said induction heater.

10. The device according to claim 1, wherein said circulation circuit has a metal melt circulating channel inside or at least attached to said first cavity, said circulating channel being ideally configured for induction heating of the molten metal.

11. The device according to claim 1, further comprising:
a second cavity being a coating pot, said first cavity is at least one metal alloy melting pot for preparing the metal melt, said melting pot connected to said second cavity; and
a metal melt conduit disposed between said first and second cavities, said circulation circuit connected to said metal melt conduit.

12. The device according to claim 1, further comprising a baffle device, and, in said first cavity, a metal melt intake by said circulation circuit is preceded by said baffle device for catching at least compounds floating on the surface of a molten bath sampled in said first cavity.

13. The device according to claim 1, further comprising a measurement chamber, an inert gas is applied to the direct measurement surface of the metal melt to protect it from oxidation reactions, a gas circulation flowrate of which ensures leakproof scavenging between said measurement chamber containing the direct measurement surface and said measuring instrument.

14. The device according to claim 1, further comprising a window of a material transparent to an ablation laser beam and to plasma radiation and disposed between said measuring instrument and the direct measurement surface so as to form a leakproof measurement chamber.

15. The device according to claim 1, wherein said measuring instrument is a spectral analysis device performing laser ablation of the direct measurement surface.

16. The device according to claim 1, further comprising a measurement chamber and the direct measurement surface is disposed in said measurement chamber made of materials that are unreactive with the metal melt.

17. The device according to claim 16, wherein said material of said measurement chamber is selected from the group consisting of an austenitic stainless steel, a ceramic and a ceramic-coated metal.

18. The device according to claim 1, wherein the circulation circuit includes a pump for sampling the metal melt at least at its intake.

19. The device according to claim 18, wherein said circulation circuit includes a pump having pumping properties coupled with isolation of impurities.

20. The device according to claim 19, wherein said pump is selected from the group consisting of an electromagnetic pump and a pump equipped with an overflow stage.

21. The device according to claim 18, wherein said pump is selected from the group consisting of electromagnetic pumps, mechanical pumps, centrifugal type pumps, pneumatic pumps and Venturi effect pump priming pumps.

22. The device according to claim 1, wherein said circulation circuit has at least one sampling intake capable of being dipped through a molten metal surface.

\* \* \* \* \*